United States Patent [19]

Collins et al.

[11] Patent Number: 5,011,914

[45] Date of Patent: Apr. 30, 1991

[54] PURIFIED CILIARY NEUROTROPHIC FACTOR

[76] Inventors: Franklin D. Collins, 582 Locust Pl., Boulder, Colo. 80302; Leu-Fen Lin, 854 Braun Ct., Golden, Colo. 80401

[21] Appl. No.: 293,851

[22] Filed: Jan. 5, 1989

[51] Int. Cl.$^5$ .................... C07K 3/14; C07K 3/18; C07K 3/24; C07K 3/28

[52] U.S. Cl. .................... 530/399; 530/412; 530/415; 530/417; 530/418; 530/419; 530/420; 530/427

[58] Field of Search ............... 530/418, 417, 412, 419, 530/399, 420, 415, 427

[56] References Cited

U.S. PATENT DOCUMENTS 4,923,696 5/1990 Appel et al. .................... 424/548

OTHER PUBLICATIONS

Scoper, R. K. 1987, *Protein Purification; Principles and Practice*, Springer Varlag, N.Y., pp. 33–35, 45–54, 93–99, 111–113, 199–208 and 285–290.

Sofer et al., 1983, *Bio Techniques*, Nov.–Dec., pp. 198–203.

Manthorpe et al., 1986, *Brain Research* 367(10:282–286.

Popiela et al., 1981, *Developmental Biology* 83:266–277.

Watters et al., 1987, *J. of Neurochemistry* 49(3): 705–713.

Mizrachi et al., 1986, i *J. of Neurochemistry*, 46(6): 1675–1682.

Bonneryia et al., 1986, *Biol Technology* 4:954–958.

*Primary Examiner*—Margaret Moskowitz
*Assistant Examiner*—Keith Furman

[57] ABSTRACT

A ciliary neurotrophic factor (CNTF), particularly sciatic nerve CNTF (SN-CNFT) is claimed. The SN-CNTF described herein is a single protein species and has a specific activity that increased to greater than 25,000-fold from crude extract. The purification is carried out by lowering the pH of the crude nerve extract preparation to form a precipitate which is removed and discarded; raising the pH to about 6.3 followed by ammonium sulfate fractionation; chromatofocusing a solution containing a second precipitate obtained from the 30% to 60% ammonium sulfate containing solution; subjecting the fractions obtained by chromatofocusing to sodium dodecyl sulfate (SDS)-polyacrylamide gel electrophoresis (PAGE); and performing reversed-phase high-performance liquid chromatography (HPLC) on the SDS-PAGE eluate.

Amino acid data for this SN-CNTF is also provided. In addition, methods for using this data for providing SN-CNTF probes and for screening cDNA and genomic libraries are also provided. Recombinant-DNA methods for the production of SN-CNTF are described.

1 Claim, 6 Drawing Sheets

↓ SAMPLE INJECTION
⊢→ START ELUTING WITH POLYBUFFER
— ABSORPTION AT 280 nm
○—○ pH
●—● CNTF ACTIVITY IN TU
⊢—⊣ FRACTIONS POOLED FOR FURTHER ANALYSIS

PURIFIED CILIARY NEUROTROPHIC FACTOR

BACKGROUND OF THE INVENTION

The present invention relates to neurotrophic factors and ciliary neurotrophic factor (CNTF) in particular, as well as methods of purifying CNTF and producing recombinant CNTF.

Severe mental and physical disabilities result from the death of nerve or glial cells in the nervous system. The death of nerve or glial cells can be caused by neurodegenerative diseases such as Alzheimer's and Parkinson's diseases and multiple sclerosis, by the ischemia resulting from stroke, by a traumatic injury, or by the natural aging process.

Neurotrophic factors are a class of molecules that promote the survival and functional activity of nerve or glial cells. Evidence exists to suggest that neurotrophic factors will be useful as treatments to prevent nerve or glial cell death or malfunction resulting from the conditions enumerated above. Appel, 1981, Ann. Neurology 10:499.

The best charaterized of such neurotrophic factors is nerve growth fractor (NGF). NGF has been demonstrated to be a neurotrophic factor for the forebrain cholinergic nerve cells that die during Alzheimer's disease and with increasing age. The loss of these nerve cells is generally considered responsible for many of the cognitive deficits associated with Alzheimer's disease and with advanced age.

Experiments in animals demonstrate that NGF prevents the death of forebrain cholinergic nerve cells after traumatic injury and that NGF can reverse cognitive losses that occur with aging. Hefti and Weiner, 1986, Ann. Neurology 20:275; Fischer et al, 1987, Nature. 329:65. These results suggest the potential clinical utility in humans of this neurotrophic factor in the treatment of cognitive losses resulting from the death of forebrain cholinergic nerve cells through disease, injury or aging.

A complication of the use of neurotrophic factors is their specificity for only those subpopulations of nerve cells which possess the correct membrane receptors. Most nerve cells in the body lack NGF receptors and are apparently unresponsive to this neurotrophic factor. It is, therefore, of critical importance to discover new neurotrophic factors that can support the survival of different types of nerve or glial cells than does NGF.

New neurotrophic factors have been searched for by their ability to support the survival in culture of nerve cells that are not responsive to NGF. One widely used screening assay is designed to discover factors that promote the survival of ciliary ganglionic motor neurons that innervate skeletal and smooth muscle. These ciliary ganglionic nerve cells belong to the parasympathetic nervous system and their survival is not supported by NGF.

The presence of factors which promote the survival of ciliary ganglionic nerve cells have been reported from a variety of tissues and species. Many of these ciliary ganglionic neurotrophic activities have the following similar chemical and biological properties: (1) the activity is present in high concentration in sciatic nerves; (2) the neurotrophic activity survives exposure to the ionic detergent sodium dodecyl sulfate (SDS) and to the reducing agents beta-mercaptoethanol (BME) or dithiothreitol (DTT) during electrophoresis on SDS polyacrylamide reducing gels; and (3) on such gels the activity migrates with an apparent molecular weight between 24-28 kd. Collins, 1985, *Developmental Biology*, 109:255-258: Manthorpe et al., 1986, *Brain Research*. 367:282-286.

Based on these similar properties, it has been proposed that the same or closely related molecules, typically referred to as "ciliary neurotrophic factor" or "CNTF", are responsible for the ciliary ganglionic neurotrophic activities. Thus, the term CNTF is an operational definition referring to agents with the above properties that promote the survival of ciliary ganglionic nerve cells in culture. Without sufficient data to establish that the proteins responsible for these activities are identical, CNTFs will be distinguished by their tissue and species of origin. Thus, if the species of origin is rabbit, the nomenclature is rabbit sciatic nerve CNTF (rabbit SN-CNTF).

Sciatic nerve CNTF is apparently found in highest concentration in peripheral nerves, such as the sciatic nerve. It is released from cells in the nerve upon injury. SN-CNTF supports the survival and growth of all peripheral nervous system nerve cells tested, including sensory, sympathetic, and parasympathetic nerve cells. Thus, SN-CNTF has a broader range of responsive nerve cells than does NGF. A rat SN-CNTF has recently been shown to regulate the formation of specific types of glial cells in the central nervous system (Hughes et al., 1988, Nature 335:70).

The most reasonable hypothesis based on the evidence cited above is that sciatic nerve CNTF is a component of the response of the nervous system to injury. SN-CNTF released from cells in a damaged nerve would be expected to promote the survival and regrowth of injured nerve cells and regulate the functional activation of glial cells necessary for regeneration. These considerations indicate that SN-CNTF would have therapeutic value in reducing damage to the nervous system caused by disease or injury.

Despite widespread scientific interest in SN-CNTF, the difficulty of purifying substantial amounts from natural sources and the unavailability of human SN-CNTF have hampered attempts to demonstrate its value in sustaining the viability of nerve cells during disease or after injury. Prior attempts to purify a rat SN-CNTF has resulted in an 800-fold enrichment over crude nerve extract in terms of specific activity. Manthorpe et al., 1986, *Brain Research* 367:282-286.

However, an eight hundred-fold increase in specific activity was insufficient to produce a single protein species. Therefore, the product showing increased activity obtained from the method described by Manthorpe et al. is insufficient as it includes multiple protein species. It would be desirable to achieve a purification of SN-CNTF such that a single protein species is obtained with the appropriate biological activity. Once a single protein species is obtained, sequencing data obtained will be more accurate. By "single protein species," as that term is used hereafter in this specification and the appended claims, is meant a polypeptide or series of polypeptides with the same amino acid sequence throughout their active sites. In other words, if the operative portion of the amino acid sequence is the same between two or more polypeptides, they are "a single protein species" as defined herein even if there are minor heterogeneities with respect to length or charge.

SUMMARY OF INVENTION

An object of the present invention is to provide an improved method of purifying SN-CNTF.

Another object of the present invention is to provide a SN-CNTF purified to an extent greater than ever achieved before, such that a single protein species is obtained.

Yet another object of the present invention is to provide probes which facilitate screening of cDNA and genomic libraries in order to clone the animal and human genes encoding SN-CNTF.

These and other objects are achieved by providing a method of purifying SN-CNTF such that specific activity is increased greater than 25,000-fold from crude extract to purified SN-CNTF. The SN-CNTF purified greater than 25,000-fold is also provided.

According to other preferred features of certain preferred embodiments of the present invention, SN-CNTF probes are provided for screening cDNA and genomic libraries for SN-CNTF.

According to other advantageous features of certain preferred embodiments of the present invention, a process of purifying SN-CNTF is provided which includes the steps of acid treatment, ammonium sulfate fractionation, chromatofocussing, running the preparation on SDS-Page gel and reverse phase-HPLC.

It is to be understood that both the foregoing general description and the following detailed description are exemplary and explanatory only, and are not restrictive of the invention, as claimed. The accompanying drawings, which are incorporated in and constitute a part of the specification, illustrate various embodiments of the invention and, together with the description, serve to explain the principles of the invention.

BRIEF DESCRIPTION OF THE DRAWINGS

FIG. 4 depicts exemplary results of a silver stained reducing SDS-Page gel run on fractions equivalent to those adjacent to and including the peak of neurotrophic activity shown in FIG. 3;

DESCRIPTION OF THE PREFERRED EMBODIMENTS

Figure 1:
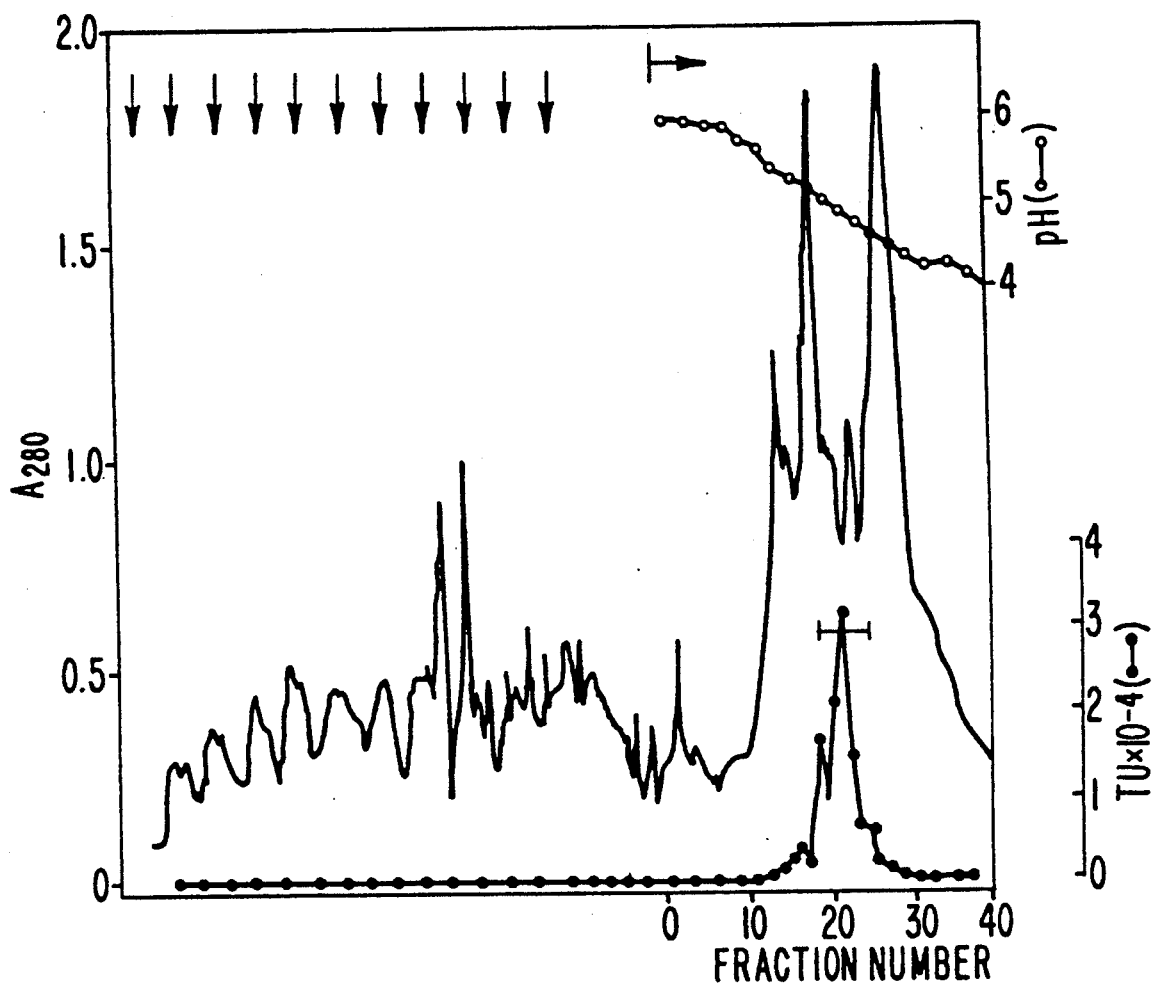
FIG. 1 depicts exemplary results of chromatography on a Mono P column.

Reference will now be made in detail to the presently preferred embodiments of the invention which, together with the following examples, serve to explain the principles of the invention.

As noted above, the present invention relates to an SN-CNTF that is purified at least 25,000-fold from crude extract. This SN-CNTF is a single protein species as that term is defined herein. As a single protein species, the amino acid sequence of the SN-CNTF may be determined and used to design DNA probes for obtaining genomic or cDNA clones for use in recombinant production of SN-CNTF.

The amino acid sequence of the single protein species of SN-CNTF has been partially determined. That sequence is:

I—R—S—D—L—T—A—L—T—E—S—

Y—V—K—H—Q—G—L—N—K—N

D—G—V—P—M—A—G

K—L—W—G—L—K

In addition, the present invention relates to an improved method of purifying SN-CNTF. While the present invention is related to SN-CNTF from any source, the description which follows will address that isolated from rabbits.

Briefly, one preferred embodiment of the present method includes pulverizing rabbit sciatic nerve material. The crude extract is then centrifuged. The supernatant is acidified and the resulting precipitate is removed by centrifugation. The supernatant is then titrated with NaOH and the resulting precipitate is again removed by centrifugation.

After pH precipitations, saturated ammonium sulfate solution is added to the supernatant and the precipitant is removed by centrifugation. With the further addition of ammonium sulfate to the supernatant, a precipitation of protein fraction containing most of the SN-CNTF activity results.

The above preparation is then loaded onto a Mono P chromatofocussing FPLC column. Column fractions are then collected and analyzed for pH and CNTF activity. The fractions indicated by a bar in FIG. 1 with peak SN-CNTF activity is then further treated as will be discussed in detail below.

The focused fractions from multiple runs over the Mono P column are electrophoresed on SDS polyacrylamide slab gel. A region of the gel corresponding to molecular weights between 22 and 27 kd is cut across the width of the gel into multiple strips. The individual strips are cut into smaller pieces and proteins are eluted electrophoretically. Eluted proteins are collected, and the fraction with the highest activity is further purified usingreverse-phase HPLC. This process is described in more detail in the Examples which follow.

The method provided by the present invention has resulted in SN-CNTF in a purified form with a greater than 25,000-fold increase in specific activity from the crude extract. Further, the final product produced is a single protein species. This represents an increase of greater than 30-fold over the SN-CNTF, which includes multiple protein species, reported as purified in Manthorpe et al. discussed above. Since SN-CNTF is partially inactivated on reverse phase HPLC, the calculation of at least 25,000-fold purification according to the present invention represents a minimum purification, and the actual purification may be even 100,000-fold or greater. This increased purification will facilitate the determination of the amino acid sequence of SN-CNTF. According to the present invention, sufficient amino acid sequence has already been obtained to generate oligonucleotide probes that will facilitate screening of cDNA and genomic libraries in order to clone the animal and human genes coding for SN-CNTF.

As will be discussed in greater detail below, these genes will in turn make possible large-scale production of (1) animal SN-CNTF suitable for studies of its ability to treat animal models of nervous system damage, and (2) human SN-CNTF suitable for inclusion in pharmaceutical formulations useful in treating damage to the human nervous system.

With these purified proteins, the amino acid sequence of the prominent peptides can be determined. The proteins are first treated with endoprotease ASP-N or endoprotease Lys-C. After digestion with endoprotease, the amino acid sequence of prominent peptides can be determined using an Applied Biosystems gas phase protein sequencer.

Antibodies that react with purified SN-CNTF can be used for screening expression libraries in order to obtain the gene which encodes SN-CNTF. Synthetic peptides can be synthesized which correspond to regions of the sequence of SN-CNTF using an Applied Biosystems automated protein synthesizer. Such peptides can be used to prepare the antibodies.

From the work above, an ultimate goal is to clone and express the human SN-CNTF gene in order to prepare material suitable for use in human pharmaceutical preparations. Once the genomic sequence is known, genes encoding SN-CNTF can then be expressed in animal cells.

The following examples are provided to illustrate certain preferred embodiments of the present invention, and are not restrictive of the invention, as claimed. All references provided in these Examples are specifically incorporated herein by reference.

EXAMPLE 1

Protein Preparation

A. Materials

Adult rabbit sciatic nerves were obtained from Pel-Freez Biologicals, Rogers, Ark. Ammonium sulfate (ultrapure) was purchased from Schwartz/Mann Biotech, Cleveland, Ohio. Phenylmethylsulfonyl fluoride (PMSF), epsilon-amionocaproic acid, benzamidine, pepstatin, dithiothreitol (DTT), poly-L-ornithine (P3655), and 3-[4,5-dimethylthiazol-2-yl]-2,5-diphenyltetrazolium bromide (MTT) were obtained from Sigma Chemical Co., St. Louis, Mo. Mono P chromatofocussing FPLC columns were obtained from Pharmacia, Inc., Piscataway, N.J. C8 reverse phase HPLC columns were obtained from Synchrom, Inc., Lafayette, Ind. Acetonitrile was purchased from J. T. Baker Chemical Co., Phillipsburg, N.J. Trifluoroacetic acid was obtained from Pierce Chemicals, Rockford, Ill. Endoproteases Asp-N and Lys-C were obtained from Boehringer Mannheim Biochemicals, Indianapolis, Ind. Fetal calf serum was purchased from Hyclone Laboratories, Logan, Utah. Culture media and salt solutions were obtained from Irvine Scientific, Santa Ana, Calif. Culture dishes were obtained from Costar, Cambridge, Mass. Utility grade pathogen-free fertile chick embryo eggs were obtained from Spafas, Roanoke, Ill.

B. Assay for SN-SNTF

Cultures of primary chick embryo ciliary ganglia were prepared as previously described (Collins, 1978, Develop. Biol. 65:50; Manthorpe et al., 1986, Develop. Brain Res. 25:191). Briefly, ciliary ganglia were removed from fertile, pathogen-free chicken eggs that had been incubated for 9-10 days at 38° C. in a humidified atmoshere. The ganglia were chemically dissociated by exposure first to Hanks' Balanced Salt Solution without divalent cations, containing 10 mM HEPES buffer pH 7.2 for 10 min at 37° C., and then by exposure to a solution of 0.125% bactotrypsin 1:250 (Difco, Detroit, Mich.) in Hanks' Balanced Salt Solution modified as above for 12 min at 37° C. Trypsinization was stopped by addition of fetal calf serum to a final concentration of 10%.

After this treatment, ganglia were transferred to a solution consisting of Dulbecco's high glucose Modified Eagle Medium without bicarbonate containing 10% fetal calf serum and 10 mM HEPES, pH 7.2 and were mechanically dissociated by trituration approximately 10 times through a glass Pasteur pipet whose opening had been fire polished and constricted to a diameter such that it took 2 seconds to fill the pipet.

The dissociated ganglia were then plated in culture medium (Dulbecco's Modified Eagle Medium supplemented with 10% fetal calf serum, 4 mM glutamine, 60 mg/L penicillin-G, 25 mM HEPES, pH 7.2) in 100 mm diameter tissue culture dishes (40 dissociated ganglia per dish) for three hours. This preplating was done in order to separate the nonneuronal cells, which adhere to the dish, from the nerve cells, which do not adhere. After three hours, the nonadherent nerve cells were collected by centrifugation, resuspended in culture medium, and plated in 50 $\mu$l per well onto half area 96 well microtiter tissue culture plates at a density of 1500 nerve cells per well. The microtiter wells had been previously exposed to a 1 mg/ml solution of poly-L-ornithine in 10 mM sodium borate, pH 8.4 overnight at 4° C., washed in distilled water and air dried.

Ten $\mu$l of a serial dilution of the sample to be assayed for neurotrophic activity was added to each well and the dishes were incubated for 20 hours at 37° C. in a humidified atmosphere containing 7.5% $CO_2$. After 18 hours, 15 $\mu$l per well of a 1.5 mg/ml solution of the tetrazolium dye MTT in Dulbecco's high glucose Modified Eagle Medium without bicarbonate containing 10 mM HEPES, pH 7.2, was added and the cultures placed back in the 37° C. incubator for 4 hours. Then, 75 $\mu$l of a solution of 6.7 ml of 12M HCl per liter of isopropanol was added and the contents of each well triturated 30 times to break open the cells and suspend the dye. The absorbance at 570 nm was determined relative to a 690 nm reference for each well using an automatic microtiter plate reader (Dynatech, Chantilly, Va.). The absorbance of wells which had not received any neurotrophic agent (negative controls) was subtracted from the absorbance of sample-containing wells. The resulting absorbance is proportional to the number of living cells in each well, defined as those nerve cells capable of reducing the dye. The number of trophic units of neurotrophic activity was defined as the reciprocal of the dilution that gave 50% of maximal survival of nerve cells. The concentration of trophic activity in trophic units per ml was obtained by dividing the total trophic units by the assay volume (60 $\mu$l). Specific activity was determined by dividing the number of trophic units by the amount of protein present in the sample.

C. Purification of SN-CNTF

At the end of each of the following steps, the preparation was either processed immediately or stored at −70° C. for up to one week until used.

Step 1. Crude Extract Preparation

One Hundred grams (wet weight) of rabbit sciatic nerve (about 300 nerves) was thawed and pulverized using a Polytron rotary homogenizer (Kinematica, Switzerland) for 1 minute in 10 volumes (wt/vol) of water containing 10 mM EDTA, 1 mM epsilon-aminocaproic acid, 1 mM benzamidine and, 0.1 mM PMSF, and centrifuged at 140,000×g for 30 minutes at 4° C. The supernatant was filtered through glass wool to remove floating lipid.

Step. 2. Acid Treatment and Ammonium Sulfate Fractionation

The centrifugation steps referred to below were performed at 17,000×g for 20 minutes and all operations were performed at 4° C., unless otherwise stated. The crude extract was centrifuged. The supernatant was acidified to pH 3.6 with 5N HCl and the resulting precipitate was removed by centrifugation. The supernatant was titrated to pH 6.3 with 1N NaOH and the resulting precipitate was again removed by centrifugation. To the above supernatant was added saturated ammonium sulfate solution to achieve 30% saturation and the precipitate was removed by centrifugation. Further addition of ammonium sulfate to the supernatant to achieve 60% saturation resulted in the precipitation of a protein fraction containing most of the SN-CNTF activity. The precipitate was dissolved in 20 mM sodium phosphate buffer, pH 6.7, containing 1 mM EDTA, 0.1 mM PMSF and 0.1 μM pepstatin, to give a protein concentration of 8-13 mg/ml.

Step 3. Chromatofocussing

The above preparation was dialyzed overnight against a 500-fold fold larger volume of 10 mM sodium phosphate, pH 67 with one change of buffer, and centrifuged at 140,000×g for 30 minutes. The supernatant was passed through 0.22 μm pore-diameter nylon filter and loaded in 3 injections of 2 ml each onto a Mono P chromatofocussing FPLC column (bed volume 4 ml) equilibrated in 25 mM bis-Tris-HCl buffer, pH 5.8. The column was washed with the same buffer until the absorbance at 280 nm of the effluent returned to baseline. The sample was then chromatographed with polybuffer, pH 4.0 (1-10 dilution of PB74 from Pharmacia).

Column fractions were collected and analyzed for pH and CNTF activity. FIG. 1 shows the results of chromatography on Mono P. The profile of eluted proteins is plotted as the optical density (O.D.) at 280 nm. Superimposed are plots of the pH and SN-CNTF activity measured in each fraction. The fractions indicated by the bar with peak SN-CNTF activity (around pH 5) were pooled and treated with solid ammonium sulfate to achieve 95% saturation and the pellet was collected by centrifugation, resuspended in saturated ammonium sulfate solution and centrifuged again to remove the polybuffer. The precipitate was dissolved in sufficient 10 mM sodium phosphate buffer, pH 6.7 to give a final protein concentration of 3-5 mg/ml (referred to as the "focussed fraction"). Typically, 1 liter of the original crude extract was processed in 8 separate runs on the Mono P column.

Step. 4. Preparative Sodium Dodecyl Sulfate (SDS) Gel Electrophoresis

The focussed fractions from multiple runs over the Mono P column were combined and dialyzed against a 100-fold larger volume of 10 mM sodium phosphate buffer, pH 6.7 for 8 hours with one change of buffer, then run on a 15% reducing SDS polyacrylamide slab gel according to the method of Laemmli, 1970. Each resolving gel measured 0.3 cm in thickness, 14 cm in height, and 11.5 cm in width. 5.5 mg of protein was loaded onto each gel. Electrophoresis was performed at 15° C. and 40 mA/gel until the 20 kd prestained molecular weight standard just reached the bottom of the resolving gel.

To reveal the curvature of individual protein bands across the width of the slab gel, the gel was overlayed with a sheet of nitrocellulose (0.45 μm pore size in roll form obtained from Millipore Corporation, Bedford, Mass.) prewetted with water, 2 sheets of prewetted and 2 sheets of dry chromatography paper (3 MM Chr obtained from Whatman, Hillsboro, Oreg.), a glass plate and a 500 ml glass bottle for weight. After 30-45 minutes, the outline of the gel was traced onto the nitrocellulose paper using a water-insoluble marker. The paper was washed 3 times with 10 mm Tris-HCl buffer, pH 8.0 containing 0.15 M NaCl and 0.3% NP-40 detergent, and then stained for 15-30 minutes with a 1:1000 dilution of Kohinuor Rapidograph Ink (available at stationary supply stores) in the above buffer.

Figure 2:
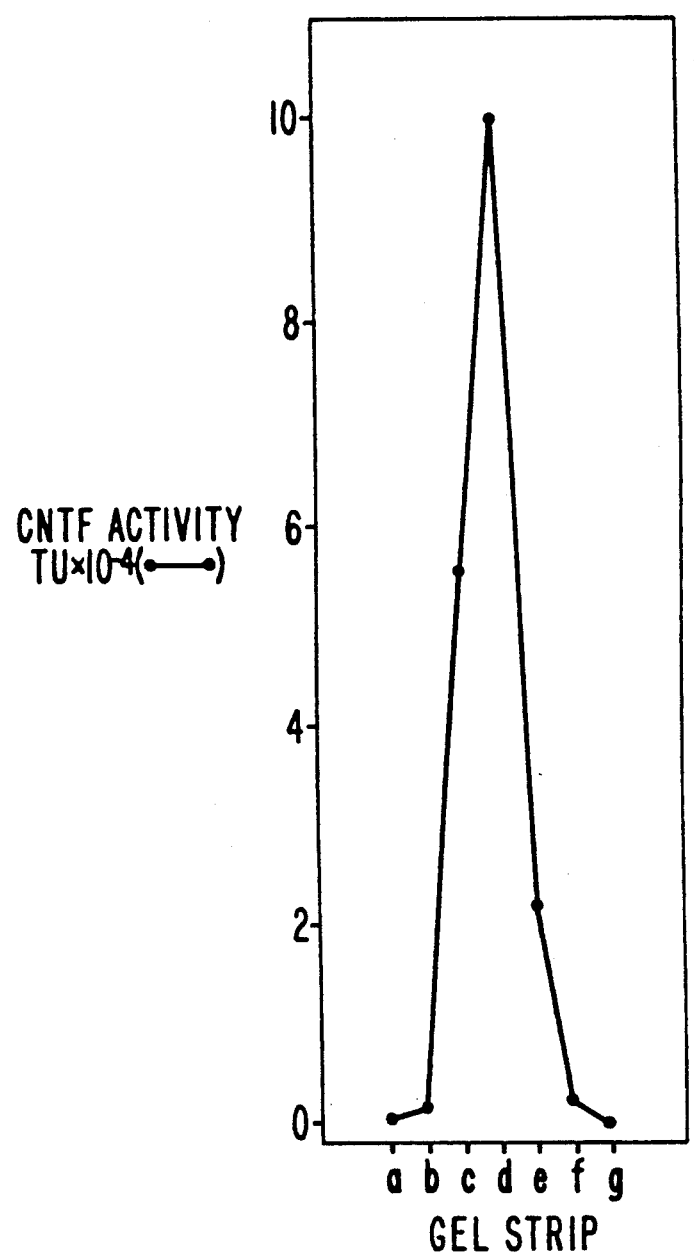
FIG. 2 depicts an exemplary plot of the distribution of neurotrophic activity in the elute from each of the seven strips cut from the SDS-Page gel after electrophoresis.

The original gel was placed onto a glass plate and aligned with its outline on the stained nitrocellulose paper underneath the glass. The region of the gel corresponding to molecular weights between 22-27 kd was located with reference to prestained molecular weight standards (BRL, Bethesda, Md.) run in narrow lanes at both ends of each gel. This region was cut across the width of the gel into seven 2.5 mm parallel strips using the banding curvature revealed by the stained nitrocellulose paper. Each individual gel strip was cut into smaller pieces (2.5×2 mm) and proteins were eluted electropohoretically for 6 hours in a 1:1 dilution of the Laemmli running buffer using an electrophoretic concentrator (ISCO, Lincoln, Nebr.). Eluted proteins were collected in a volume of 0.2 ml. FIG. 2 plots the distribution of neurotrophic activity in the elute from each of the 7 strips (labelled a-g in order of decreasing molecular weight). The fraction with the highest activity (strip d) was further purified using reverse-phase HPLC.

Step 5. Reverse Phase—HPLC

Figure 3:
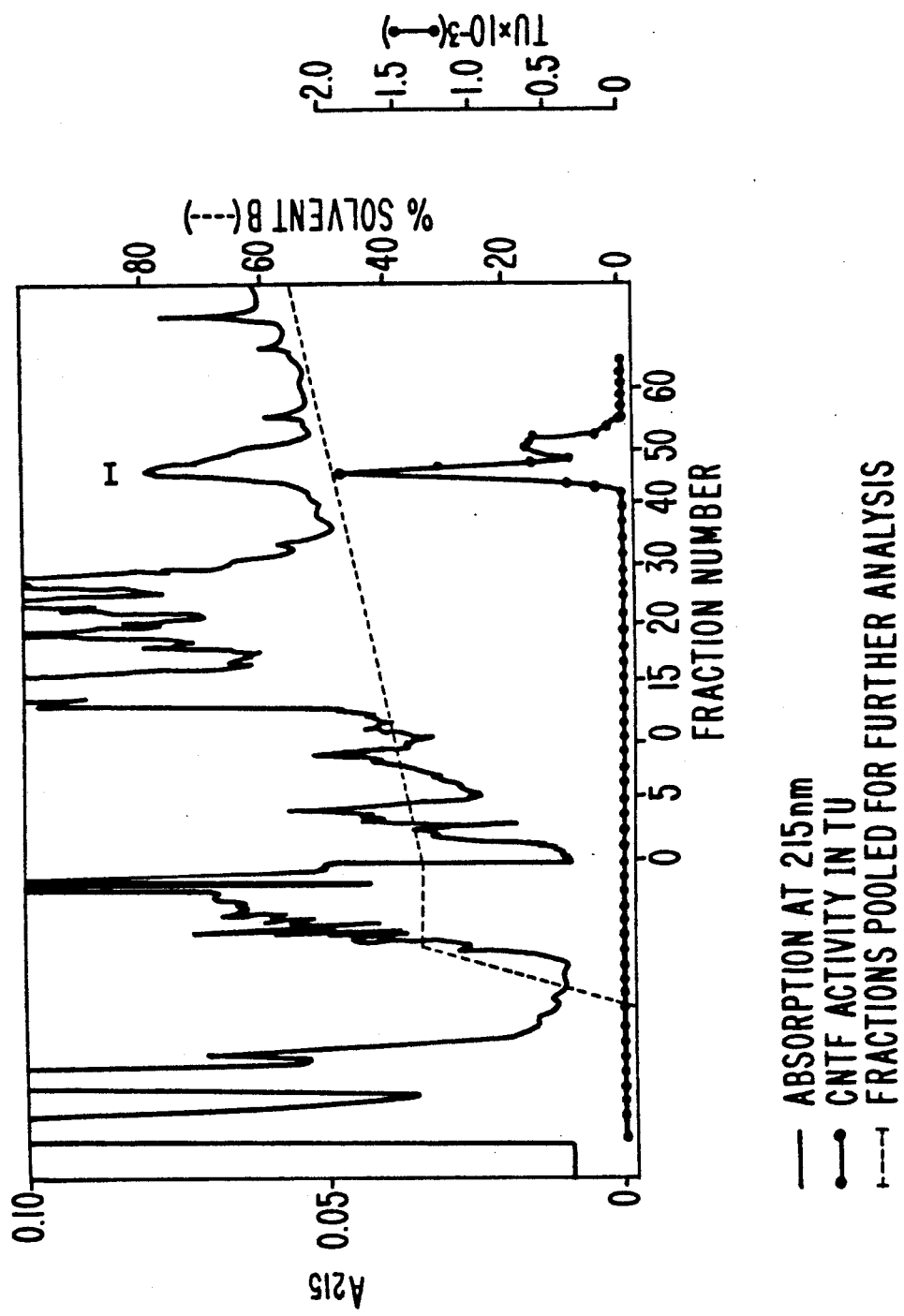
FIG. 3 depicts exemplary results of reverse phase chromatography.
Figure 4:
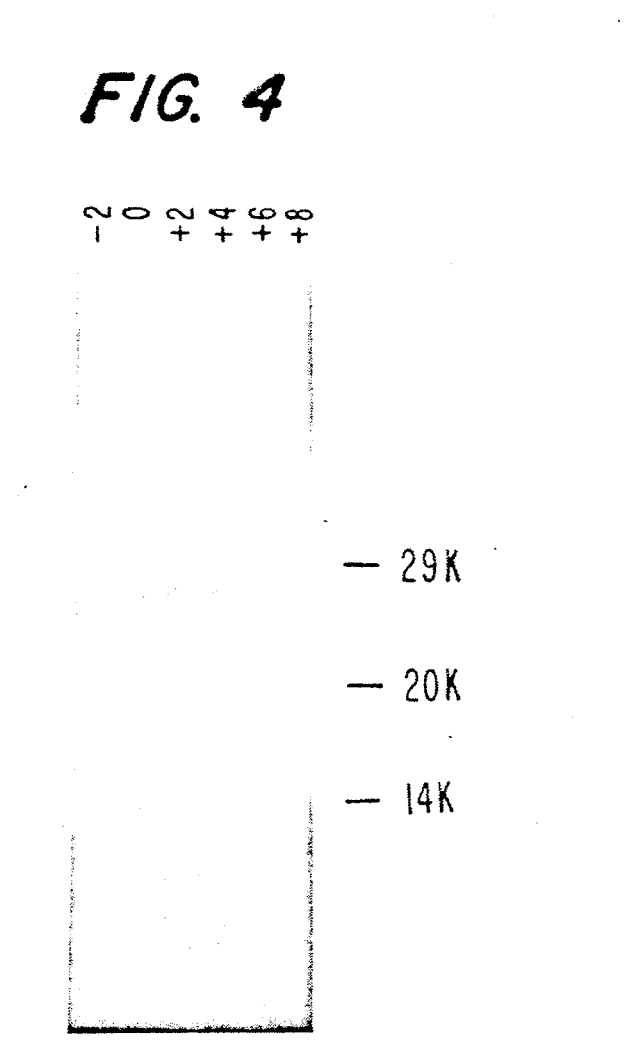

Dithiothreitol (DTT) and 10% trifluroacetic acid (TFA) were added to the gel eluate to achieve final concentrations of 2% and 0.3%, respectively. The sample was filtered through a 0.22 μm nylon filter, loaded onto a C8 reverse phase HPLC column and eluted with an $H_2O$/0.1% TFA:acetonitrile/0.1% TFA gradient. Fractions were collected into siliconzied tubes containing 5 μl of 0.4% Tween 20 detergent. Aliquots from each fraction were assayed for neurotrophic activity. FIG. 3 shows the results of reverse phase chromatography. Protein concentration is indicated by absorbance at 215 nm and the distribution of neurotrophic activity is superimposed. Fractions with the peak SN-CNTF activity (fractions 37-40, FIG. 3) were pooled for sequencing as described in Example 2. In a separate preparation, fractions adjacent to and including the peak CNTF activity, equivalent to fractions 36-44 in FIG. 3, were also analyzed on silver-stained reducing SDS-PAGE (FIG. 4).

EXAMPLE 2

Sequencing of the Purified Neurotrophic Factor

Figure 5:
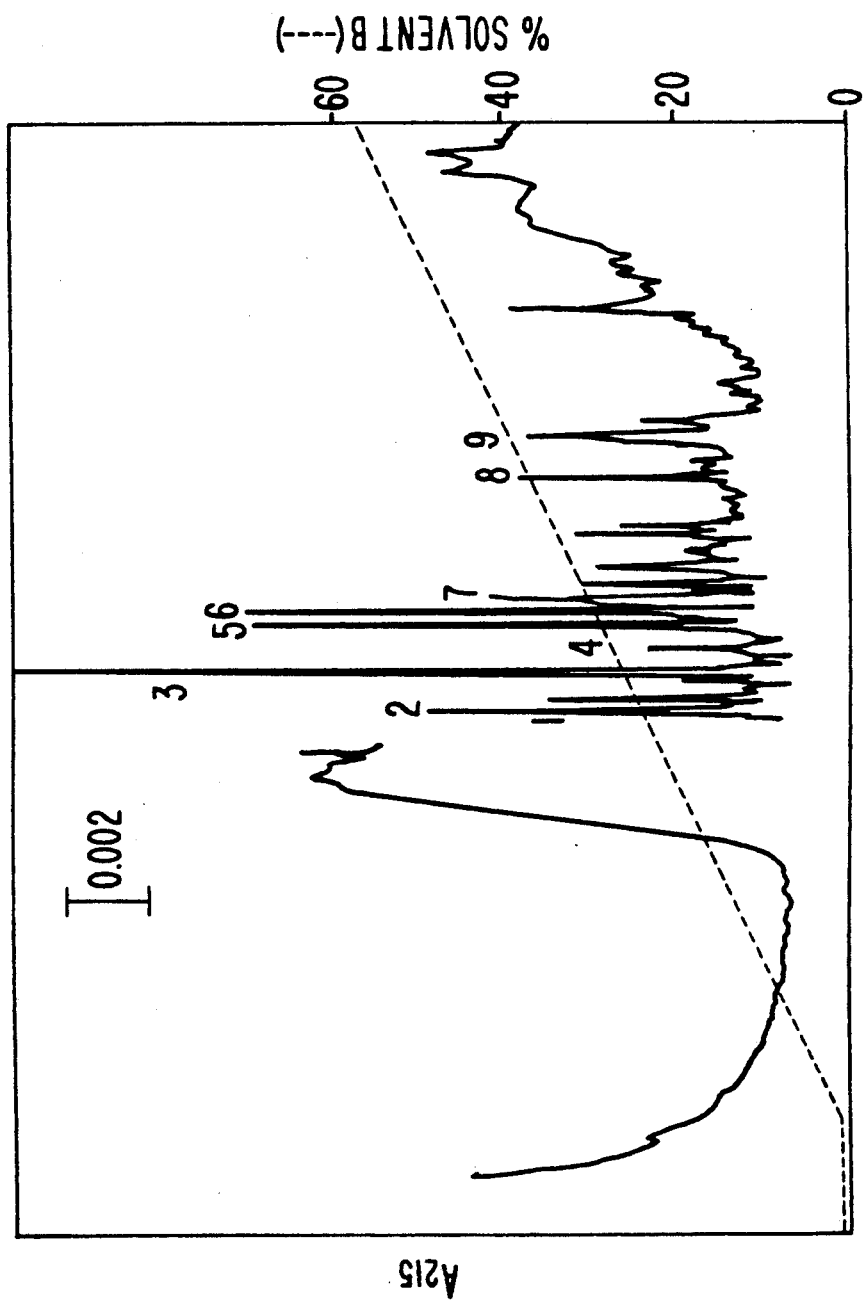
FIG. 5 depicts a profile of eluted peptides after digestion with endoprotease Asp-N.
Figure 6:
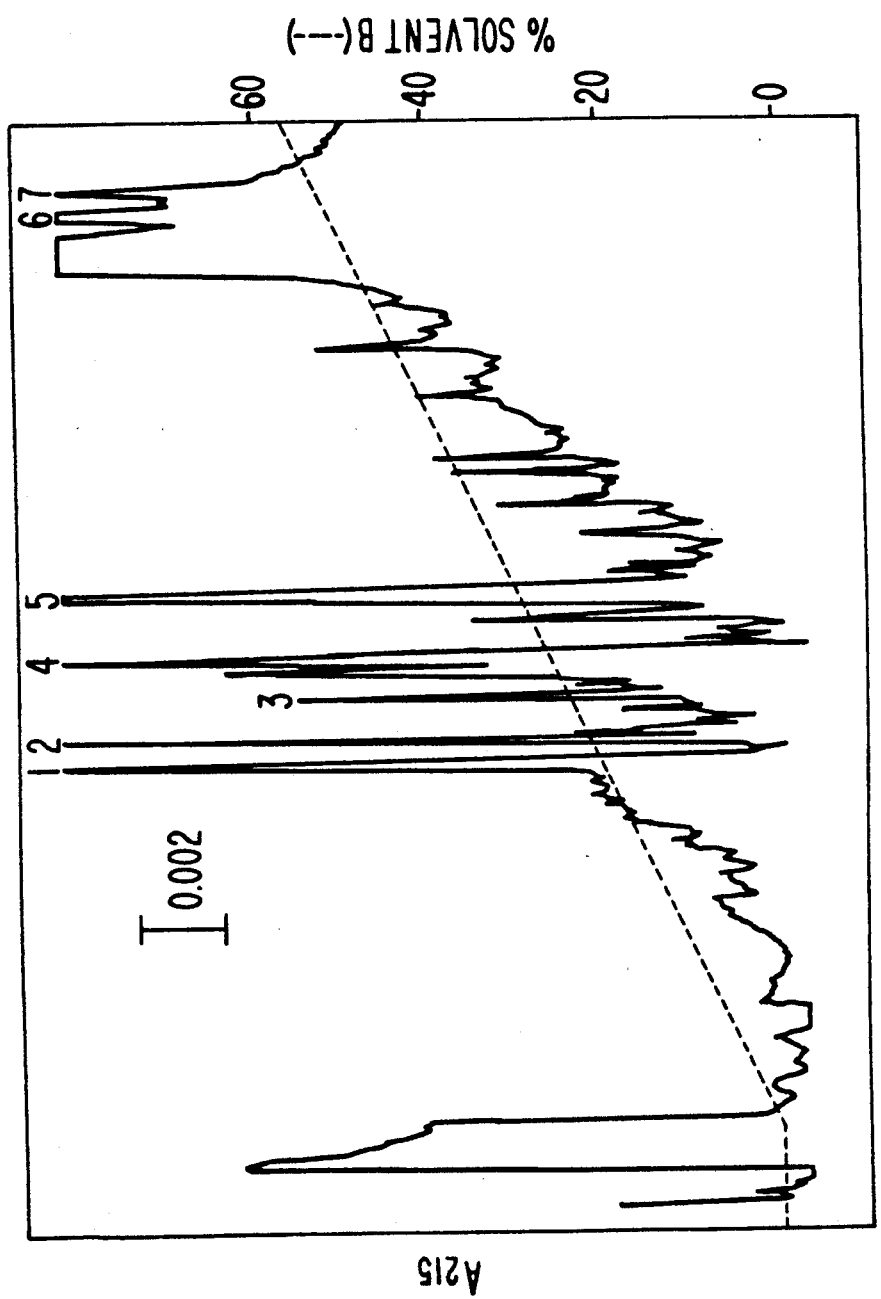
FIG. 6 depicts a profile of eluted peptides after digestion with endoprotease Lys-C.

Fractions with the peak SN-CNTF activity (#37-40, FIG. 3) were pooled and concentrated to 50 μl on a vacuum evaporator centrifuge. The concentrated sample contained 0.14% Tween 20. It was diluted with 1% ammonium bicarbonate to a final volume of 350 μl and treated with endoprotease Asp-N or endoprotease Lys-C overnight at 37° C. The mixture was concentrated to approximately 50-100 μl on a vacuum evaporator centrifuge and loaded via a 1 ml sample loop onto a narrow bore Aguapore RP-300 C8 reverse phase HPLC column (Brownlee Labs), 2.1×220 mm, eluted with an $H_2O$/0.1% TFA: acetonitrile/0.1% TFA gradient. Peptide containing fractions were collected manually into Eppendorf tubes based on the absorption at 215 nm. FIG. 5 shows the profile of eluted peptides after digestion with endoprotease Asp-N as determined by absorbance at 215 nm. FIG. 6 shows the profile of eluted peptides after digestion with endoprotease Lys-C followed by reduction and carboxymethylation. The amino acid sequence of the prominent peptides was determined using an Applied Biosystems gas phase protein sequencer.

EXAMPLE 3

Preparation of Antibodies to the Neurotrophic Factor

Antibodies that react with purified rabbit SN-CNTF will be useful for screening expression libraries in order to obtain the gene which encodes rabbit SN-CNTF. In addition, antibodies that neutralize its biological activity will be used in intact animals in order to determine the biological role of this neurotrophic factor.

In order to prepare such antibodies, synthetic peptides will be synthesized which correspond to regions of the sequence of SN-CNTF using an Applied Biosystems automated protein synthesizer. Such synthetic peptides will be covalently linked to the carrier protein keyhole limpet hemocyanin. The conjugated peptide will be injected into guinea pigs in complete Freund's adjuvant, with booster shots applied at 3 and 6 weeks in incomplete adjuvant. Serum samples will be taken from each guinea pig and used in a Western blot against purified SN-CNTF in order to determine if antibody in the serum reacts with the purified protein. Sera positive in the Western assay will be further tested for ability to neutralize the neurotrophic activity in the bioassay used for purification. Sera positive in either the Western or neutralization assay will be further purified as follows: (1) the sera will be absorbed with the carrier protein keyhole limpet hemocyanin in order to remove antibodies directed against that protein, then the sera will be retested i the above assays; (2) the IgG antibody fraction will be purified from the serum by standard procedures and retested in the above assays. Both these steps will provide a polyclonal antibody that is pure enough to be used to screen expression libraries in order to clone the messenger RNA and gene for SN-CNTF.

EXAMPLE 4

Cloning the Gene for SN-CNTF

The ultimate goal of the work to be described is to clone and express the human SN-CNTF gene in order to prepare material suitable for use in human pharmaceutical preparations. Since the peptide sequences obtained are for rabbit SN-CNTF and the rabbit and human sequences may not be identical, it is prudent to first obtain clones of the rabbit gene via hybridization with synthetic oligonucleotides based on the protein sequence and to employ the rabbit clones as hybridization probes in screens for the human gene.

Both the genomic and messenger RNA (mRNA) sequences encoding rabbit and human SN-CNTF will be obtained. The mRNA sequence will be useful for expressing the protein, whereas the genomic sequence will be essential for understanding the structure and regulation of the gene for SN-CNTF. In order to obtain these sequences, both rabbit and human genomic libraries and rabbit and human cDNA libraries made from mRNA isolated from sciatic nerves will be screened. In the process of obtaining the gene corresponding to the sequence of abbit or hu an SN-CNTF, it is also possible to screen for structurally closely related genes that may represent additional members of this family of neurotrophic factors.

A. SN-CNTF Gene

To isolate the rabbit genomic sequences encoding SN-CNTF, a rabbit genomic library (Clontech) will be plated on the *E.coli* nm538 bacterial strain and approximately 1,000,000 recombinant clones will be screened. Regions of the protein sequence of rabbit SN-CNTF that can be represented by the fewest codons will be reverse-translated and corresponding degenerate oligonucleotide probes will be synthesized. The rabbit oligonucleotides will be labeled by kinasing according to the standard protocol of Maniatis et al. (1982, Molecular Cloning, A Laboratory Manual, Cold Spring Harbor Laboratory). The DNA kinase is obtained from US Biochemical Corp. and the gamma-labeled ATP is obtained from ICN. Oligonucleotides will be labeled to a specific activity of at least 1,000,000 cpm per picomole.

Upon plating of the genomic libary, approximately 1 million plaques will be transferred onto dupliate nitrocellulose filters. The filters will then be processed according to the methods of Maniatis et al. (1982, ibid.) and hybridized overnight with radioactively-labeled oligonucleotide probe. The hybridization cocktail will include 6× SSCP, 2× Denhardt's, 0.05% sodium pyroophosphate, 1 mM EDTA, 0.1% SDS, 100 μg yeast tRNA (Sigma), pH 8.0. The temperature of hybridization will be several degrees below the calculated Tm of the oligonucleotide. Clones that hybridize with several probes based on different regions of the protein sequence will be plaque purified and the regions of hybridization will be sequenced by dideoxy termination method (Sanger et al., 1977, Proc. Natl. Acad. Sci. 74:5463) using Sequenase (US Biochemicals Corp.) in order to identify those clones that encode the SN-CNTF protein sequence.

B. SN-CNTF mRNA Sequences

Total cellular RNA will be obtained from rabbit and human sciatic nerves. The tissue will be homogenized in a guanidinium thiocyanate/beta-mercaptoethanol solution and the RNA will be purified by sedimentation through cesium chloride gradients (Glison et. al., 1974, Biochemistry 13:2633). Polyadenylated RNA will be selected by chromatography on oligo(dT)cellulose (Avid and Leder, 1972, Proc. Natl. Acad. Sci. 69:408). Quantitative RNA blot hybridization analysis will be performed with "antisense" oligonucleotide probes to estimate the prevalence of SN-CNTF sequences in each RNA preparation and to thereby estimate the number of independent clones one would need to screen to have at least a 99% probability of obtaining CNTF clones. Sufficient doublestranded complimentary DNA will be synthesized as described by Gubler and Hoffman, 1983, Gene 25:263, and inserted into the lambda gem2 vector (Promega Biotech) according to Palazzolo and Myerowitz, 1987, Gene 52:197.

Rabbit SN-CNTF encoding clones will be identified by hybridization of recombinant phage plaques as described above. The identities of the clones will be verified by determination of nucleotide sequences in order to determine correspondence with the entire known protein sequence. Screens of the human sciatic nerve cDNA library will be conducted with randomly-primed rabbit SN-CNTF cDNA probes (Feinberg and Vogelstein, 1983, Anal. Biochem. 132:6), which is a more reliable procedure for detecting cross-species hybridization than the use of the smaller oligonucleotides used to screen the rabbit cDNA libraries.

EXAMPLE 5

Expression of Genes Encoding SN-CNTF in Animal Cells

Animal-cell expression of SN-CNTF requires the following steps:
a. Construction of an expression vector;
b. Choice of a host cell line;
c. Introduction of the expression vector into host cells; and Manipulation of recombinant host lls to increase expression levels of SN-CNTF.

(a) SN-CNTF expression vectors designed for use in animal cells can be of several types including strong constitutive expression constructs, inducible gene constructs, as well as those designed for expression in particular cell types. In all cases, promoters and other gene regulatory regions such as enhancers (inducible or not) and polyadenylation signals are placed in the appropriate location in relation to the cDNA sequences in plasmid-based vectors. Two examples of such constructs follow: (1) A construct using a strong constitutive promoter region should be made using the simian virus 40 (SV40) gene control signals in an arrangment such as that found in the plasmid pSV2CAT as described by Gorman et al. in Mol. Cel. Biol. 2:1044–1051, 1982, specifically incorporated herein by reference. This plasmid should be manipulated in such a way as to substitute the SN-CNTF cDNA for the chloramphenicol acetyltransferase (CAT) coding sequences using standard molecular biological techniques (Maniatis et al., supra). (2) An inducible gene construct should be made utilizing the plasmid PMK which contains the mouse metallothionein (MT-1) promoter region (Brinster et al., Cell 27:228–231, 1981). This plasmid can be used as a starting material and should be manipulated to yield a metal-inducible gene construct.

(b) A number of animal cell lines should be used to express SN-CNTF using the vectors described above to produce active protein. Two potential cell lines that have been well-characterized for their ability to promote foreign gene expression are mouse Ltk− and Chinese hamster ovary (CHO) dhfr− cells, although expression of SN-CNTF is not limited to these cell lines.

(c) Vector DNA should be introduced into these cell lines using any of a number of gene-transfer techniques. The method employed here involves the calcium phosphate-DNA precipitation technique described by S. L. Graham and A. S. van der Eb (Virology 2:456–467, 1973) in which the expression vector for SN-CNTF is co-precipitated with a second expression vector encoding a selectable marker. In the case of Ltk− cell transfection, the selectable marker is a thymidine kinase gene and the selection is as described by Wigler et al. in Cell 16:L777–785, 1979 and in the case of CHO dhfr− cells, the selectable marker is dihydrofolate reductase (DHFR) whose selection is as described by Ringold et al. in J. Mol. Appl. Genet. 1:165–175, 1981.

(d) Cells that express the SN-CNTF gene constructs should then be grown under conditions that will increase the levels of production of SN-CNTF. Cells carrying the metallothionein promoter constructs can now be grown in the presence of heavy metals such as cadmium which will lead to a 5-fold increased utilization of the MT-1 promoter (Mayo et al., Cell 29:99–108) subseguently leading to a comparable increase in SN-CNTF protein levels. Cells containing SN-CNTF expression vectors (either SV40- or MT-1-based) along with a DHFR expression vector can be taken through the gene amplification protocol described by Ringold et al. in J. Mol. Apl. Genet. 1:165:175, 1981, using methotrexate, a competitive antagonist of DHFR. This leads to more copies of the DHFR genes present in the cells and, concomitantly, increased copies of the SN-CNTF genes which, in turn, can lead to more SN-CNTF protein beingproduced by the cells.

EXAMPLE 6

Purification of SN-CNTF from Recombinant Animal Cells

Since SN-CNTF is expected to be synthesized by cells like the natural material, it is anticipated that the methods described above for purification of the natural protein will allow similar purification and characterization of the recombinant protein.

It will be apparent to those skilled in the art that various modifications and variations can be made in the processes and products of the present invention. Thus, it is intended that the present invention cover the modifications and variations of this invention provided they come within the scope of the appended claims and their equivalents. Also, the term SN-CNTF is intended to encompass all origins of species, unless the term is immediately preceded by a specific origin of species.

What is claimed is:

1. A method for purifying sciatic nerve ciliary neurotrphic factor and the specific activity of said factor by at least about 25,000 fold from crude sciatic nerve extract comprising:
   lowering the pH of the crude nerve extract to form a first precipitate;
   removing and discarding said first precipitate from the lowered pH extract;
   raising the pH of said extract to about 6.3;
   adding ammonium sulfate to the raised pH extract;
   chromatofocusing a solution containing a second precipitate obtained from the 30% to 60% ammonium sulfate containing solution;
   subjecting fractions obtained by chromatofocusing to sodium dodecyl sulfate polyacrylamide gel electrophoresis; and
   performing reversed-phase high-performance liquid chromatography on the sodium dodecyl sulphate polyacrylamide gel electrophoresis eluate.

* * * * *

UNITED STATES PATENT AND TRADEMARK OFFICE
CERTIFICATE OF CORRECTION

PATENT NO. : 5,011,914
DATED : April 30, 1991
INVENTOR(S) : Franklin D. Collins, et al Page 1 of 2

It is certified that error appears in the above-indentified patent and that said Letters Patent is hereby corrected as shown below:

Column 1, line 23, Replace "charaterized" with -- characterized --

Column 4, line 44, replace "usingreverse" with -- using reverse --

Column 5, line 57, replace "SNTF" with -- CNTF --

Column 5, line 65, replace "atmoshere" with -- atmosphere --

Column 7, line 30, replace "ph 67" with -- ph 6.7 --

Column 8, line 16, replace "Kohinuor" with -- Kohinoor --

Column 8, line 29, "electropohoretically" should read electrophoretically --

UNITED STATES PATENT AND TRADEMARK OFFICE
CERTIFICATE OF CORRECTION

PATENT NO. : 5,011,914
DATED : April 30, 1991
INVENTOR(S) : Franklin D. Collins, et al It is certified that error appears in the above-indentified patent and that said Letters Patent is hereby corrected as shown below:

Column 8, line 44, replace "siliconzied" with -- siliconized --

Column 9, line 43, replace "i" with -- in --

Column 10, line 4, replace "abbit or hu an" with -- rabbit or human --

Column 10, line 26, replace "dupliate" with -- duplicate --

Column 11, line 19, replace "lls" with -- cells --

Column 11, line 57, replace "2:456-467 with -- 52:456-467 --

Column 12, line 12, replace "subseguently" with -- subsequently --

Column 12, line 23, replace "beingproduced" with -- being produced" --

Column 12, line 43-44, replace "neurotrphic" with -- neurotrophic --

Signed and Sealed this

Twelfth Day of April, 1994

Attest:

BRUCE LEHMAN

Attesting Officer

Commissioner of Patents and Trademarks